(12) United States Patent
Hanke et al.

(10) Patent No.: US 6,822,034 B2
(45) Date of Patent: Nov. 23, 2004

(54) ANTI-MICROBIAL SILICONE RUBBER COMPOSITION AND METHOD FOR MAKING SAME

(76) Inventors: Bernhard Hanke, Breslaoerstrasse 12, Bad Schwalbach (DE), D-65307; Tim Bast, Bahnstrasse 13C, Schwalbach am Taunus (DE), D-65824

(*) Notice: Subject to any disclaimer, the term of this patent is extended or adjusted under 35 U.S.C. 154(b) by 0 days.

(21) Appl. No.: 10/017,992

(22) Filed: Dec. 14, 2001

(65) Prior Publication Data

US 2002/0082340 A1 Jun. 27, 2002

Related U.S. Application Data

(63) Continuation-in-part of application No. PCT/US00/16750, filed on Jun. 16, 2000.

(30) Foreign Application Priority Data

Jun. 17, 1999 (EP) .............................. 99111729

(51) Int. Cl.[7] ................................ C08K 3/08
(52) U.S. Cl. ................. 524/439; 524/440; 524/588; 524/386; 524/267; 524/268
(58) Field of Search ................ 524/267, 268, 524/386, 439, 440, 588; 424/618

(56) References Cited

U.S. PATENT DOCUMENTS 4,054,139 A * 10/1977 Crossley ..................... 604/265
4,677,143 A * 6/1987 Laurin et al. ................ 424/618
4,849,223 A * 7/1989 Pratt et al. ................... 424/409
6,121,298 A * 9/2000 Sakamoto et al. ........... 514/359
6,267,782 B1 * 7/2001 Ogle et al. ................... 623/1.1
2002/0115873 A1 * 8/2002 Sturmann et al. ........... 549/534
2002/0122832 A1 * 9/2002 Hanke et al. ................ 424/618

FOREIGN PATENT DOCUMENTS

JP       2000095976 A * 4/2000 ............ C09D/5/14

OTHER PUBLICATIONS

Abstract for "Plasma Enhanced Deposition of Silver Nanoparticles onto Polymer and Metal Surfaces for the Generation of Antimicrobial Characteristics" Journal of Applied Polymer Science (2004) 93(3), 1411–1422.*

* cited by examiner

Primary Examiner—Margaret G. Moore
Assistant Examiner—Marc S. Zimmer
(74) Attorney, Agent, or Firm—Lott & Friedland

(57) ABSTRACT

An anti-microbial, curable silicone rubber composition and method for making same, comprising in at least a portion of the exposed surface of said composition an organic matrix containing homogeneously dispersed particles of metallic silver having a particle size in the range of 1 to 50 nm (silver nanoparticles) in an amount providing on the surface of said composition an anti-microbially effective but less than cytotoxic silver concentration.

14 Claims, No Drawings

ANTI-MICROBIAL SILICONE RUBBER COMPOSITION AND METHOD FOR MAKING SAME

CLAIM OF PRIORITY

This application is a continuation-in-part of European Patent Office application Serial No. 99111729.2 filed on Jun. 17, 1999 and Patent Cooperation Treaty ("PCT") application Serial No. PCT/US00/16750 filed Jun. 16, 2000, based upon which priority is claimed pursuant to 35 U.S.C. §§ 102 and 365(c).

TECHNICAL FIELD

The present invention relates to a curable, anti-microbial silicone rubber composition.

BACKGROUND OF THE INVENTION

Silicone rubber compositions have been widely used in industry for a wide variety of different applications. These applications include for example pan grips, camera eye caps, handles of bicycles, slipping preventors for spectacles, various rubber sheets and rubber coated cloth such as sheets and curtains that are used for example in hospitals. Silicone rubber compositions are further used as tubes and backings for food containers or various kinds of hygienic appliances. In many of these applications, there is a demand for anti-microbial and anti-fungal efficacy of the silicone rubber compositions. This demand stands from the fact that many of the usage environments are prone to microbial or fungal contamination. For example, such usage environments include the presence of contaminated surfaces such as to and/or the presence of ambient wetness in combination with room or even higher temperatures.

In Japanese patent application 7-65149, filed on Feb. 28, 1995, it has been suggested to incorporate into a silicone rubber composition and inorganic anti-microbial agent, the agent comprising silver loaded on an inorganic material such as a zeolite, a zirconium phosphate, or a calcium phosphate. Such silicone 30 rubber compositions, however, are only capable of releasing the silver atoms in ionic form and hence are cytotoxic.

It is therefore an object of the present invention to provide a silicone rubber composition, which overcomes the disadvantages of the prior art silicone rubber compositions.

It is a further object of the present invention to provide a silicone rubber composition, which is anti-microbial by releasing silver atoms.

It is a further object of the present invention to provide a silicone rubber composition, which is anti-microbially effective whilst not being cytotoxic.

SUMMARY OF THE INVENTION

The present invention provides an anti-microbial, curable silicone rubber composition comprising in at least a portion of the exposed surface of said composition an organic matrix containing homogeneously dispersed particles of metallic silver having a particle size in the range of 1 to 50 nm (silver nanoparticles) in an amount providing on the surface of said composition an anti-microbially effective but less than cytotoxic silver concentration.

The present invention further provides a silicone rubber composition, characterized by comprising said silver nanoparticles in an amount providing a silver concentration of from more than 1 nmol/l to less than 1 $\mu$mol/l on at least a portion of the surface of said composition.

The present invention further provides a silicone rubber composition, characterized in that said organic matrix comprises said silver nanoparticles in an amount of 1 to 2000 ppm, preferably 5 to 1000 ppm and more preferably 10 to 250 ppm.

The present invention further provides a silicone rubber composition characterized by comprising silver nanoparticles having a particle size of 2 to 20 nm preferably 5 to 10 nm.

The present invention further provides a silicone rubber composition characterized in that said fluid organic matrix comprises an organic fluid wherein said silver nanoparticles are dispersed.

The present invention further provides a silicone rubber composition characterized in that said viscous organic fluid comprises an aliphatic or aromatic hydrocarbon, a mineral oil, petrolatum, glycerol, a fatty alcohol, polypropylene lo glycol, an animal and/or vegetable oil or fat, or a silicone oil.

The present invention further provides a method for manufacturing a curable, anti-microbial silicone rubber composition comprising the steps of:

providing a curable silicone rubber composition in a configuration ready for mixing providing a liquid organic matrix comprising metallic silver having a particle size in the range of 1 to 50 nm mixing said liquid organic matrix into said silicone rubber composition—optionally curing the mixture of said composition with said organic matrix

DESCRIPTION OF THE PREFERRED EMBODIMENTS

It has been surprisingly found that the anti-microbial silicone rubber composition of the present invention shows an excellent anti-microbial and fungicidal activity by not providing any cytotoxicity and is active against a broad range of microbes without any indication of resistance because of the very small quantities of silver released from the surface of said silicone rubber composition over a long period. Based on this the body care product of the present invention is ideally suited for applications, wherein said composition is used under conditions which allow for proliferation of microbes and fungi.

For the purpose of the present invention, anti-microbial efficacy, i.e. activity against a broad range of microbes, may be quantified for example by methods such as described in *Der Erlanger Silberkatheter: In-vitro Ergebnisse zur antimikrobiellen Wirksamkeit* in Infection 26 (1998) Suppl. 1, German edition, pages 25 through 31.

For the purpose of the present invention, cytotoxicity may be quantified for example by methods such as described in *Untersuchung der akuten Zytotoxizität des Erlanger Silberkatheters zur Bestimmung der Biokompatibilität* in Infection 26 (1998) Suppl. 1, German edition, pages 36 through 39.

According to a preferred embodiment of the present invention, said silver nanoparticles are dispersed in said silicone rubber matrix in such an amount that a silver concentration of from more than 1 nmol/l to less than 1 $\mu$mol/l is provided, specifically when in contact with aqueous fluids present on the surface the composition of the present invention.

Preferably at least the exposed surfaces of the silicone rubber composition of the present invention comprises said silver nanoparticles in an amount from 1 to 2000 ppm, preferably from 5 to 1000 ppm and more preferably from 10 to 250 ppm.

The silver nanoparticles homogeneously dispersed in said silicone rubber matrix preferably have a particle size of at least 2 nm, more preferably of at least 5 nm. In addition, the dispersed silver nanoparticles preferably have a particle size of not more than 20 nm, more preferably not more than 10 nm, most preferably not more than 8 nm. The silicone rubber matrix into which said silver nanoparticles then are homogeneously dispersed can be solid or fluid. The term fluid includes liquid and semisolid and covers a viscosity range of from 5 to 5000 mPa, preferably 5 to 500 mPa measured at 60° C. using a rotational viscosimeter (such as a Brookfield viscosimeter) at 60 rpm using a number 2 spindle.

According to one embodiment of the present invention, at least the exposed surfaces of the silicone rubber composition of the present invention comprise a fluid organic matrix wherein said silver nanoparticles are homogeneously dispersed. Said fluid organic matrix preferably is a viscous organic fluid having a viscosity as referred to above and comprises preferably aliphatic or aromatic hydrocarbon, a mineral oil, petrolatum, glycerol, a fatty alcohol, propylene glycol, polypropylene glycol, an animal and/or vegetable oil or fat or a silicone oil. Specifically preferred are silicone oils, i.e. polysiloxanes such as phenylfunctional-polymethylsiloxane compounds having a viscosity at 37° C. ranging from 5 to 5000 mPa, more preferably 5 to 2000 mPa, as measured with the viscosimeter preferred to above at a temperature of 37° C. A suitable silicone oil is available from Dow Corning Corporation, Michigan, USA, under the designation DC556 poly dimethyl silicone cosmetic grade (Dimethicone).

The incorporation of the silver nanoparticles can be done with an apparatus such as disclosed in German patent number 4440521 using a method involving the vacuum evaporation of metallic silver on a liquid in a vacuum chamber in which the organic fluid flows along the outside of a cylinder. This allows for the preparation of a liquid organic matrix comprising a homogenous extremely fine dispersion of silver nanoparticles having a particle size of about 5 nm. This silver-containing liquid organic matrix can be used to either coat the part of the body care product of the present invention contacting the skin and/or to impregnate or to incorporate by kneading into the material providing said surface, made of for example polyvinylbenzol, polyethylene, polypropylene or creamy oligomers, such as white petrolatum.

A suitable liquid rubber composition comprises 100 weight parts of organopolysiloxane rubber where of the average unit is represented by

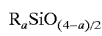

(wherein R is a substituted or non-substituted monovalent hydrocarbon radical and 'a' is between 1.95 and 2.05), 10–100 weight parts wet silica with a specific surface area of 50 square meters per gram or more, and a sufficient quantity of a hardening agent.

In principle, all silicone rubber compositions known in the art can be rendered anti-microbial and anti-fungal by the means described herein.

EXAMPLE

A suspension containing silver nanoparticles with an individual size range of 5 to 50 nm was produced through thermal evaporation of silver into a liquid silicone oil base. The silicone oil containing the silver nanoparticles was then incorporated into a silicone rubber composition obtained by addition condensation and crosslinking providing a children comfort.

The children comfort or silencer demonstrated anti-fungal and antibacterial efficacy when containing 50 ppm silver nanoparticles when directly added into one component before crosslinking. The samples were placed on (non-nutrient) mineral salt agar and inoculated with a mixed fungal spore suspension of Aspergillus niger and Penicillium pinophilium, Chaetomium globosum, Aureobasidium pullulans and Gliocladium virens. After an incubation of 28 days at 28° C. no growth of any of the microorganism was observed.

What is claimed is:

1. An anti-microbial, curable silicone rubber composition comprising a homogeneous mixture of silicone rubber, an organic matrix and particles of metallic silver having a particle size in the range of 1 to 50 nm (silver nanoparticles) in an amount providing in said composition an anti-microbially effective but less than cytotoxic silver concentration.

2. The silicone rubber composition according to claim 1, characterized by comprising said silver nanoparticles in an amount such that after curing an anti-microbially effective but less than cytotoxic silver concentration of from more than 1 nmol/l to less than 1 μmol/l is provided on at least a portion of the surface of said cured silicone rubber composition.

3. The silicone rubber composition according to claim 2, characterized in that said organic matrix comprises said silver nanoparticles in an amount of 1 to 2000 ppm.

4. The silicone rubber composition according to claim 3, characterized by comprising silver nanoparticles having a particle size of 2 to 20 nm.

5. The silicone rubber composition according to claim 1, characterized in that said organic matrix comprises an organic fluid wherein said silver nanoparticles are dispersed.

6. The silicone rubber composition according to claim 5, characterized in that said organic fluid is selected from the group consisting of: aliphatic hydrocarbons, aromatic hydrocarbons, mineral oils, petrolatum, glycerol, fatty alcohols, polypropylene glycol, animal oils, vegetable oils, silicone oils and combinations thereof.

7. A method for manufacturing a curable, anti-microbial silicone rubber composition comprising the steps of:

providing a curable silicone rubber composition in a configuration ready for mixing;

providing an organic matrix comprised of an organic fluid, said organic matrix having particles of metallic silver with a particle size in the range of 1 to 50 nm dispersed therein;

combining said organic matrix and said silicone rubber composition;

optionally curing the combination of said silicone rubber composition and said organic matrix.

8. The silicone rubber composition according to claim 3, characterized by comprising silver nanoparticles having a particle size of 5 to 10 nm.

9. The silicone rubber composition according to claim 2, characterized in that said organic matrix comprises said silver nanoparticles in an amount of 5 to 1000 ppm.

10. The silicone rubber composition according to claim 9, characterized by comprising silver nanoparticles having a particle size of 2 to 20 nm.

11. The silicone rubber composition according to claim 9, characterized by comprising silver nanoparticles having a particle size of 5 to 10 nm.

12. The silicone rubber composition according to claim 2, characterized in that said organic matrix comprises said silver nanoparticles in an amount of 10 to 250 ppm.

13. The silicone rubber composition according to claim 12, characterized by comprising silver nanoparticles having a particle size of 2 to 20 nm.

14. The silicone rubber composition according to claim 12, characterized by comprising silver nanoparticles having a particle size of 5 to 10 nm.

* * * * *